(12) United States Patent
Bonczar et al.

(10) Patent No.: US 10,293,093 B2
(45) Date of Patent: May 21, 2019

(54) MOBILE EXTRACORPOREAL LIFE SUPPORT SYSTEMS AND RELATED METHODS

(71) Applicant: ZOLL LifeBridge GmbH, Ampfing (DE)

(72) Inventors: Michael Bonczar, Ampfing (DE); Thomas Bauer, Eggenfelden (DE); Jeremy Thomas Dabrowiak, Santa Clara, CA (US); Werner Hestner, Zangberg (DE)

(*) Notice: Subject to any disclaimer, the term of this patent is extended or adjusted under 35 U.S.C. 154(b) by 730 days.

(21) Appl. No.: 14/807,732

(22) Filed: Jul. 23, 2015

(65) Prior Publication Data

US 2017/0021080 A1  Jan. 26, 2017

(51) Int. Cl.
| | |
|---|---|
| A61M 1/00 | (2006.01) |
| A61M 1/16 | (2006.01) |
| A61M 1/36 | (2006.01) |
| A61G 12/00 | (2006.01) |

(52) U.S. Cl.
CPC ......... *A61M 1/1698* (2013.01); *A61G 12/008* (2013.01); *A61M 1/3626* (2013.01); *A61M 1/3643* (2013.01); *A61M 1/3666* (2013.01); *A61M 1/3667* (2014.02); *A61M 1/3601* (2014.02); *A61M 2205/502* (2013.01); *A61M 2209/082* (2013.01); *A61M 2209/084* (2013.01); *A61M 2209/086* (2013.01)

(58) Field of Classification Search
CPC . A61G 12/008; A61M 1/1698; A61M 1/3601; A61M 1/3667; A61M 1/36; A61M 1/3626; A61M 1/3666; B60R 22/22
See application file for complete search history.

(56) References Cited

U.S. PATENT DOCUMENTS

| | | | | |
|---|---|---|---|---|
| 5,391,030 A | * | 2/1995 | Lee | A61G 3/0808 410/12 |
| 5,803,324 A | * | 9/1998 | Silberman | B62D 43/04 224/42.23 |
| 6,179,175 B1 | * | 1/2001 | Painter | A45F 3/08 224/153 |
| 7,367,540 B2 | | 5/2008 | Brieske | |
| 7,597,546 B2 | | 10/2009 | Brieske | |
| 7,682,327 B2 | | 3/2010 | Kirchhof | |
| 7,846,122 B2 | | 12/2010 | Brieske | |
| 8,187,214 B2 | | 5/2012 | Brieske et al. | |
| 8,529,488 B2 | | 9/2013 | Brieske | |

(Continued)

FOREIGN PATENT DOCUMENTS

| | | |
|---|---|---|
| WO | WO2012/058778 A2 | 5/2012 |
| WO | WO2012/059890 A1 | 5/2012 |

OTHER PUBLICATIONS

O Maunz et al., "Bridge to Life: The LifeBridgeB2T(R) Extracorporeal Life Support System in an In Vitro Trial," Perfusion, vol. 23, No. 5, Sep. 1, 2008, pp. 279-282.

(Continued)

*Primary Examiner* — Ariana Zimbouski
(74) *Attorney, Agent, or Firm* — Robert D. Buyan; Stout, Uxa & Buyan, LLP

(57) ABSTRACT

Extracorporeal life support (ECLS) systems, devices and methods wherein a portable ECLS device is used to deliver cardiovascular support to a humans or animal patient (or harvested organ(s)) during pre-hospital or inter-hospital transport.

20 Claims, 16 Drawing Sheets

(56) References Cited

U.S. PATENT DOCUMENTS

| | | | |
|---|---|---|---|
| 8,568,347 B2 | 10/2013 | Brieske et al. | |
| 8,721,579 B2 | 5/2014 | Muller-Spanka et al. | |
| 8,834,399 B2 | 9/2014 | Muller-Spanka et al. | |
| 8,844,336 B2 | 9/2014 | Sagebiel | |
| 8,882,693 B2 | 11/2014 | Muller-Spanka et al. | |
| 8,951,220 B2 | 2/2015 | Brieske et al. | |
| 2003/0103831 A1* | 6/2003 | Alderman | B60P 3/079 410/100 |
| 2004/0155628 A1* | 8/2004 | Liscio | A61B 5/0046 320/127 |
| 2009/0121592 A1* | 5/2009 | De Nando | A61B 19/0248 312/209 |
| 2011/0208108 A1* | 8/2011 | Muller-Spanka | A61M 1/1698 604/6.09 |
| 2012/0143115 A1 | 6/2012 | Muller-Spanka et al. | |
| 2013/0088348 A1* | 4/2013 | Verachtert | B60R 22/48 340/457.1 |
| 2014/0142491 A1 | 5/2014 | Brieske | |
| 2014/0326678 A1 | 11/2014 | Arzt et al. | |
| 2015/0056601 A1 | 2/2015 | Muller-Spanka et al. | |
| 2015/0073335 A1 | 3/2015 | Muller-Spanka et al. | |
| 2015/0082863 A1 | 3/2015 | Sagebiel | |
| 2015/0141897 A1 | 5/2015 | Muller-Spanka et al. | |
| 2015/0196709 A1* | 7/2015 | Jacobson | A61M 5/14244 604/67 |

OTHER PUBLICATIONS

PCT International Search Report dated Mar. 1, 2017 in related PCT Application No. PCT/IB2016/001213.

* cited by examiner

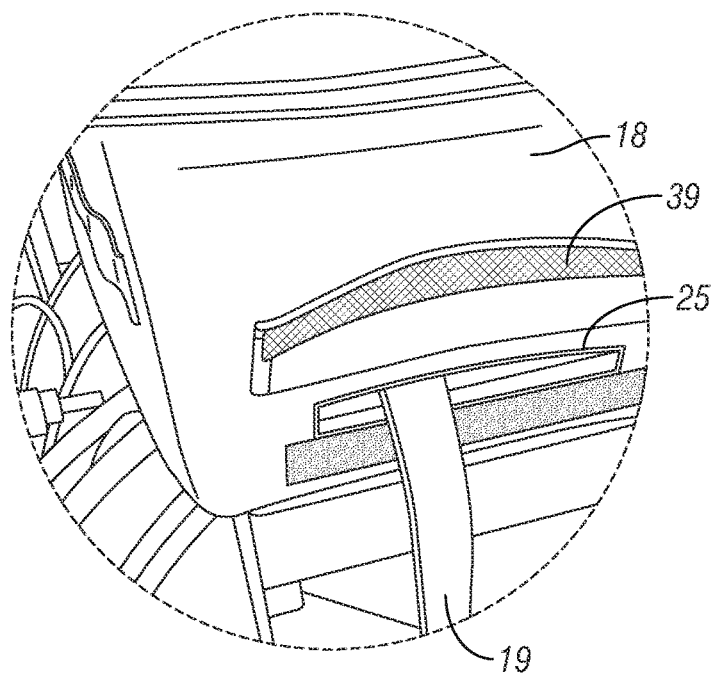
FIG. 2AA
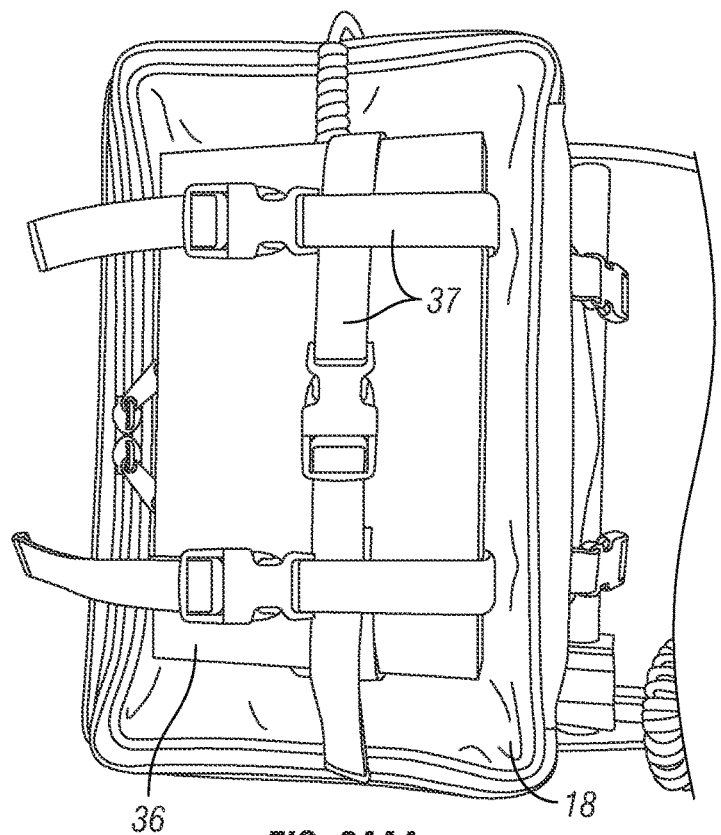
FIG. 2AAA

MOBILE EXTRACORPOREAL LIFE SUPPORT SYSTEMS AND RELATED METHODS

TECHNICAL FIELD

The present application relates generally to the fields of medicine and biomedical engineering and more particularly to devices and methods for performing cardiopulmonary bypass in human or non-human animal subjects.

BACKGROUND

Pursuant to 37 CFR 1.71(e), this patent document contains material which is subject to copyright protection and the owner of this patent document reserves all copyright rights whatsoever.

In extracorporeal life support (ECLS), blood is removed from a subject's circulatory system and channeled through an ECLS system wherein the blood becomes oxygenated and carbon dioxide is removed. The oxygenated blood is then delivered back into the subject's circulatory system. Most ECLS systems include pumps which propel or circulate the blood through the subject's vasculature thereby assuming the function of both the heart and lungs, even if the subject's heart is stopped or beating inefficiently. Other ECLS systems (e.g., the Novalung System, Novalung GmbH, Heilbronn, Germany) provide pumpless extracorporeal lung assist by oxygenating and removing carbon dioxide from the blood while relying on the subject's beating heart to adequately circulate the blood through the device and through the subject's vasculature.

In general, ECLS techniques include extracorporeal membrane oxygenation (ECMO) as well as cardiopulmonary bypass (CPB). ECMO is essentially a form of partial CPB. ECMO is typically used for extended periods of time (e.g., days) while CPB is used for relatively short periods (e.g., hours). CPB has traditionally been used during cardiac and aortic surgical procedures wherein the heart is stopped. Generally, in ECMO vascular access is achieved by inserting cannulas into peripheral blood vessels using percutaneous technique or superficial surgical cut and then advancing the cannulas to locations in the central vasculature (e.g., vena cava, right atrium, aorta). In CPB vascular access is typically accomplished by intraoperative connection of cannulas to intrathoracic blood vessels.

ECMO can be performed either as venoarterial ECMO (VA-ECMO) or venovenous ECMO (VV-ECMO). In VA-ECMO, deoxygenated blood is removed from a vein and the oxygenated blood is returned into an artery. In VA-ECMO the system typically pumps the blood under pressure to partially support the subject's cardiac output while VV-ECMO generally provides extracorporeal lung assist but does not support cardiac function.

In the past, ECLS systems were typically available only at major medical centers where specialized personnel (e.g., cardiothoracic surgeons and/or perfusionists) could be called upon to set up and operate the ECLS systems. Patients in the field, or those who presented at smaller hospital emergency departments, after suffering severe cardiac events or lung injuries would typically have to undergo (and survive) transport by vehicle (e.g., ground ambulance, helicopter, etc.) to a major medical center before having any possibility of ECLS treatment.

In recent years, efforts have been made to develop small, automated, simplified, portable ECLS systems that could be used to deliver ECLS treatment to patients at smaller hospitals and during transport, without the need for specialized personnel. Examples of such devices include those described in U.S. Pat. Nos. 7,367,540; 7,597,546; 7,682,327; 7,846,122; 8,529,488; 8,529,488; 8,187,214; 8,568,347; 8,951,220; 8,834,399; 8,882,693; 8,721,579 and 8,844,336 as well as United States Patent Application Publication Nos. US2014/0142491; US2014/0326678 US2015/0056601; US2015/0141897; US2015/0073335 and US2015/0082863, the entire disclosure of each such patent and patent application being expressly incorporated herein by reference.

SUMMARY

Various embodiments described herein provide certain advances and improvements for portable ECLS systems aimed at enhancing their automated set up and/or operation as well as their mobility and use in transport vehicles (e.g., ambulances, helicopters, watercraft, etc.)

An ECLS system which comprises an extracorporeal life support device having an inlet connectable to the vasculature of a human or animal subject or harvested organ(s), an outlet also connectable to the vasculature of the subject or organ(s) and gas exchange apparatus operable to a) receive deoxygenated blood from the vasculature of the subject or organ(s) via the inlet, b) oxygenate the blood and c) infuse the oxygenated blood into the vasculature of the subject or organ(s) via the outlet is described herein. One or more of the following components may be provided separately or in combination with an ECLS system:

a) a transport accessory kit comprising apparatus useable during transport of the subject or organ(s) while receiving treatment from the extracorporeal life support device;

b) a clinical accessory kit comprising apparatus useable while the subject or organ(s) is/are receiving treatment from the extracorporeal life support device;

c) securement member(s) or anchoring belt or strap assemblies for securing the extracorporeal life support device to a floor or other surface in a transport vehicle such as a wheeled vehicle (ground ambulance, rescue or military vehicle), aircraft (helicopter or fixed wing aircraft) or watercraft (rescue boat, military landing craft, etc.)

d) a wheeled cart for transporting the extracorporeal life support device over a floor, road or other substantially horizontal surface (e.g., from a location inside a hospital to a waiting transport vehicle); and e) a controller programmed to perform controlled start up pre-testing of the extracorporeal life support device and to issue separate error signals to indicate different types of errors detected during the start up pre-testing.

Methods for preparing, testing and using ECLS systems of the foregoing character, including a method for using a transport vehicle to transport a subject or harvested organ(s) from a first location to a second location while the subject or organ(s) is/are receiving treatment from the extracorporeal life support system are described herein.

In certain embodiments, a system or device comprising a conduit that is connectable to a subject's body, a controller, a pump and a sensor which senses pressure or flow within the conduit and transmits indicia of the sensed pressure or flow to the controller; wherein the pump creates negative pressure within the conduit to thereby withdraw a body fluid from the subject's body through the conduit, and the controller is programmed to determine when the sensed pressure or flow has fallen below a predetermined minimum and to thereafter issue control signals to the pump causing the pump to slow or stop until the sensed pressure or flow has risen above the predetermined minimum is provided. Such device or system may in some embodiments comprise an ECLS device or system in which the withdrawn body fluid is blood. However, this aspect or feature may be utilized in many other types of devices and systems including but not limited to apheresis systems and devices, autotransfusion systems and devices, hemodialysis systems and devices, hemofiltration systems and devices, plasmapheresis systems and devices and photophoresis systems and devices.

In other embodiments, there is provided an extracorporeal device having a conduit, a pump, a monitoring unit, a controller and a bubble sensor, wherein the pump circulates fluid through the conduit; the bubble sensor senses when a gas-liquid transition occurs within the conduit; the bubble sensor transmits a signal to at least the monitoring unit when a gas-liquid transition is sensed and the monitoring unit is programmed to issue an alarm or notification in response to the sensing of a gas-liquid transition by the bubble sensor; the controller is programmed to cause the system to take at least one remedial action in response to the sensing of a gas-liquid transition by the bubble sensor; and the controller is further programmed to perform a system test and a bubble sensor test while the conduit is initially being primed with fluid and/or during priming of the conduit with fluid and to provide a bubble sensor test failure indication and a system test failure indication; wherein the bubble sensor test failure indication is separate from the system test failure indication. In some embodiments a single gas-liquid transition occurs in the conduit during priming of the conduit and the bubble sensor test is timed to detect that single gas-liquid transition. In other embodiments, multiple gas liquid transitions may occur during priming of the conduit and the bubble sensor test is timed to detect at least one of those gas-liquid transitions. In some embodiments, gas may be volitionally introduced into the conduit (e.g., through a gas bubble injector) to create at least one gas-liquid transition for purposes of conducting the bubble sensor test. In at least some embodiments, the bubble sensor test and system test are performed sequentially as opposed to concurrently.

Still further aspects and details of the present invention will be understood upon reading of the detailed description and examples set forth herebelow.

BRIEF DESCRIPTION OF THE DRAWINGS

The following detailed description and examples are provided for the purpose of non-exhaustively describing some, but not necessarily all, examples or embodiments, and shall not limit the scope of the invention in any way.

FIG. 2AA is an enlarged view of region 2AA of FIG. 2A with a cover flap on the transport accessory kit lifted to reveal the manner in which a strap is used to attach the transport accessory kit to the extracorporeal life support device.

FIG. 2AAA is a top view of the transport accessory kit portion of the system of FIG. 2A showing the manner in which the DC power supply is operatively positioned on top of the transport accessory kit and held in place by DC power supply securement belts.

DETAILED DESCRIPTION

The following detailed description and the accompanying drawings to which it refers are intended to describe some, but not necessarily all, examples or embodiments of the invention. The described embodiments are to be considered in all respects only as illustrative and not restrictive. The contents of this detailed description and the accompanying drawings do not limit the scope of the invention in any way.

Figure 1A:
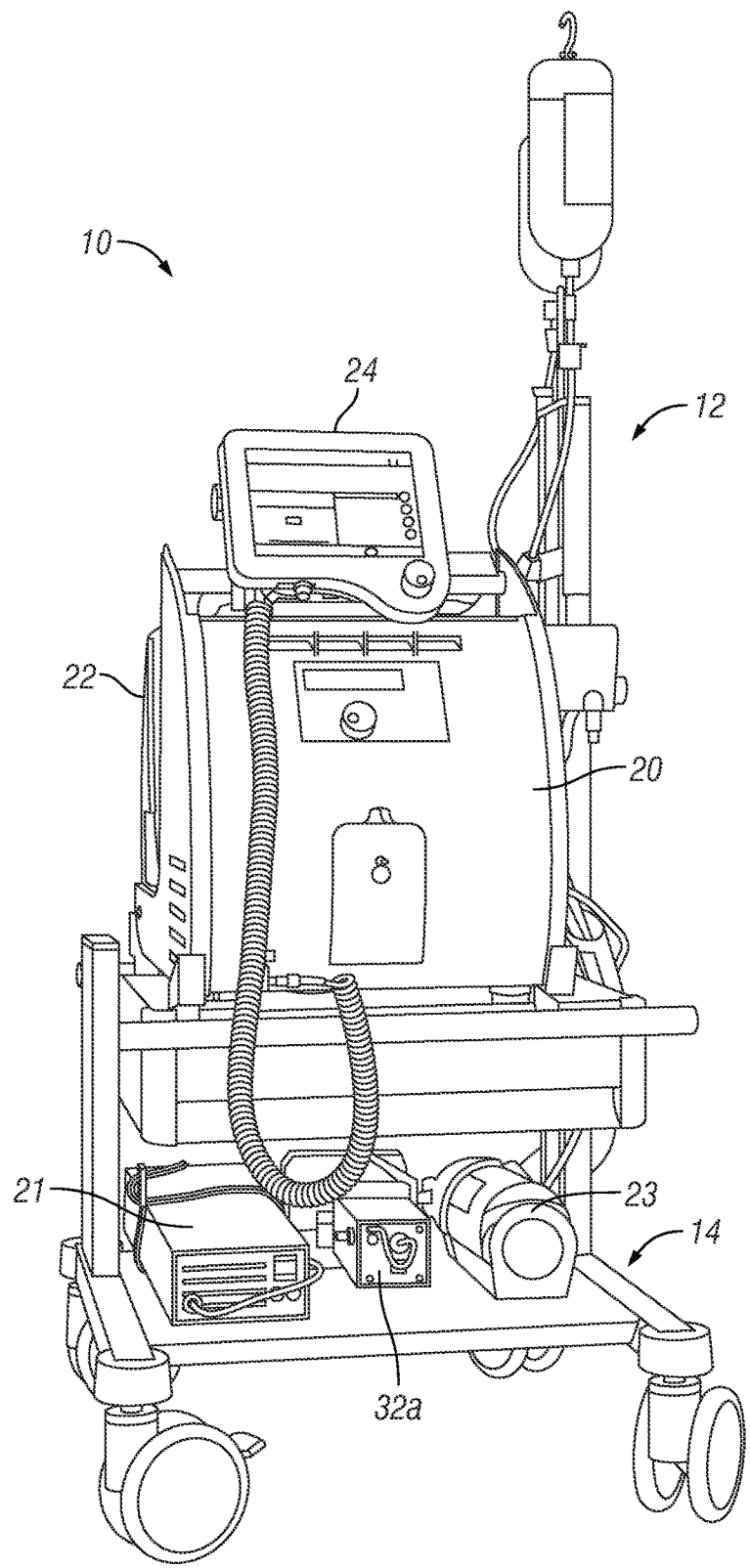
FIG. 1A is a perspective view of one embodiment of an ECLS system which includes an extracorporeal life support device positioned on a cart along with several accessory devices.

FIG. 1A shows a system 10 comprising an ECLS device 12 positioned on a cart 14 along with an AC power supply 21, an emergency derive apparatus 32a and a gas bottle 23. In this example, the ECLS device 12 generally comprises a reusable base module 20 and a disposable patient module 22.

Figure 3:
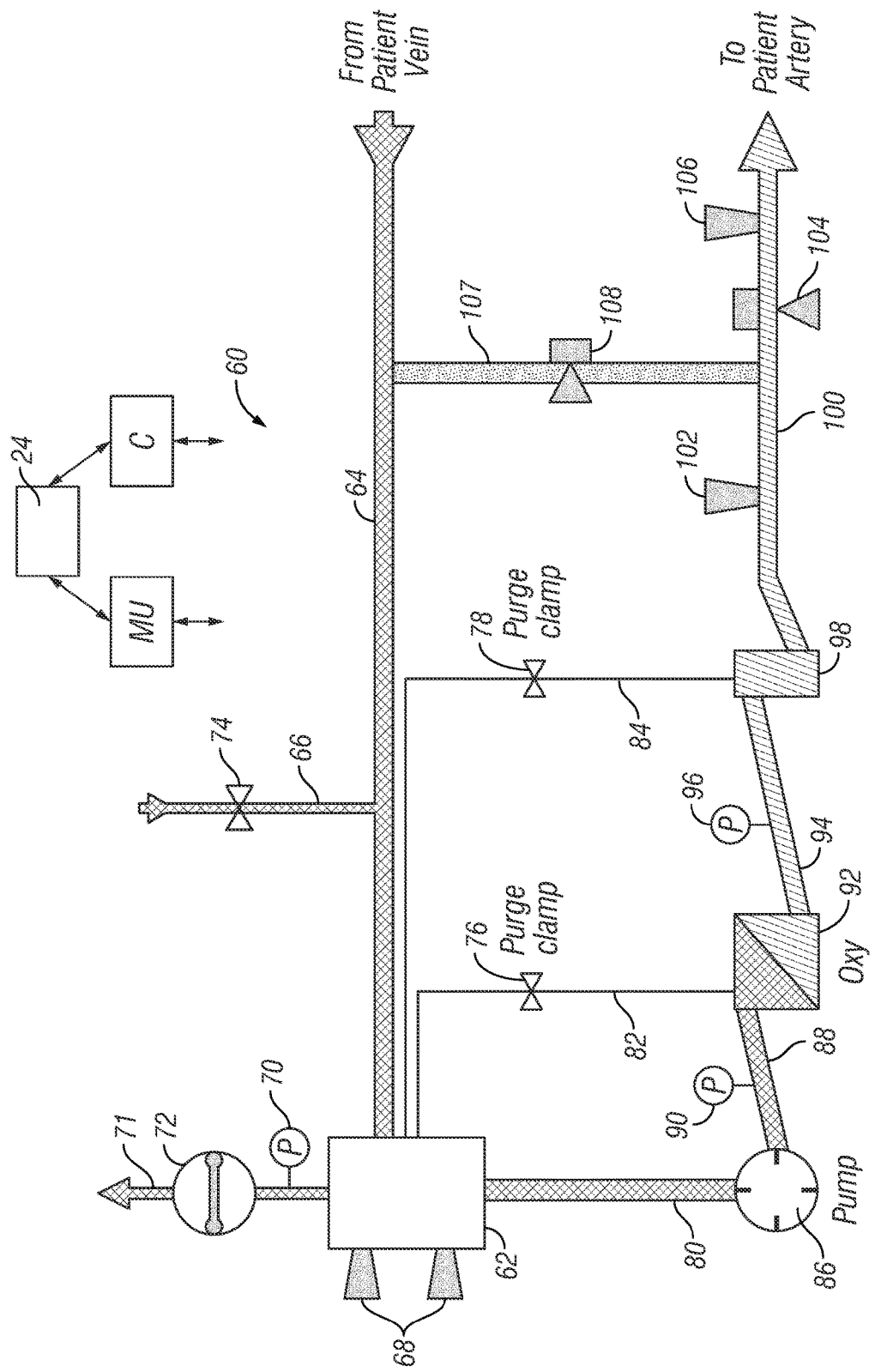
FIG. 3 is a schematic flow path and component diagram of one embodiment of an extracorporeal life support device.

The ECLS device 12 is useable for providing oxygenated blood to a human or animal subject or to vascularized organ(s) that have been explanted from a human or animal donor for subsequent transplantation (e.g., heart, lungs, heart & lungs, kidney, etc.). As described more fully below, the ECLS device includes, at minimum, an inlet which is connectable to vasculature of the subject or organ(s), an outlet which is also connectable to vasculature of the subject or organ(s) and gas exchange apparatus operable to oxygenate blood. In operation, the oxygenation apparatus receives deoxygenated blood from the subject or organ(s) via the inlet. The blood then becomes oxygenated by the oxygenation apparatus and the oxygenated blood then returns, via the outlet, into the vasculature of the subject or organ(s). In its most basic form, the ECLS device 12 is useable for VV-ECMO and other forms of extracorporeal lung assist. However, in many embodiments this ECLS device 10 may also include non-pulsatile or pulsatile blood pumping apparatus useable to propel or circulate the blood through the device 10 and through the vasculature of the subject or organ(s). The inclusion of such pumping apparatus will render the ECLS device 12 useable for full circulatory support procedures, such as VA-ECMO and CPB, as well. The ECLS device 12 may optionally include numerous other components, some examples of which are seen in the diagram of FIG. 3 and described below, and may be controlled by a programmable controller which communicates with a user interface 24, such as an LCD display. Non-limiting examples of apparatus useable as the ECLS device 12 include those described in at least some of the above-incorporated U.S. Pat. Nos. 7,367,540; 7,597,546; 7,682,327; 7,846,122; 8,529,488; 8,529,488; 8,187,214; 8,568,347; 8,951,220; 8,834,399; 8,882,693; 8,721,579 and 8,844,336 as well as United States Patent Application Publication Nos. US2014/0142491; US2014/0326678 US2015/0056601; US2015/0141897; US2015/0073335 and US2015/0082863.

Figure 1B:
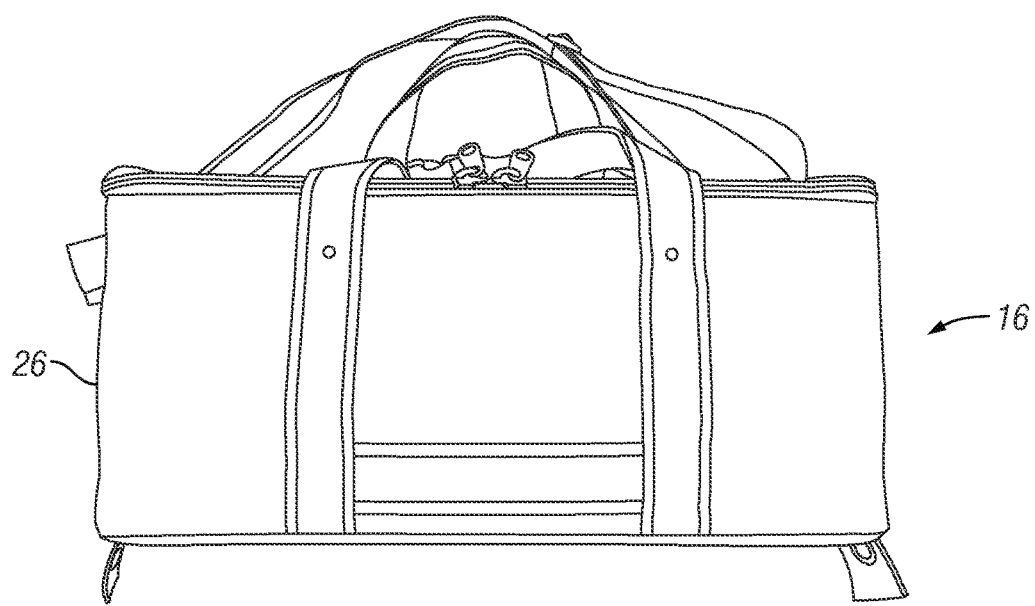
FIG. 1B is a side view of a clinical accessory kit that may optionally be included in the system of FIG. 1A.
Figure 1C:
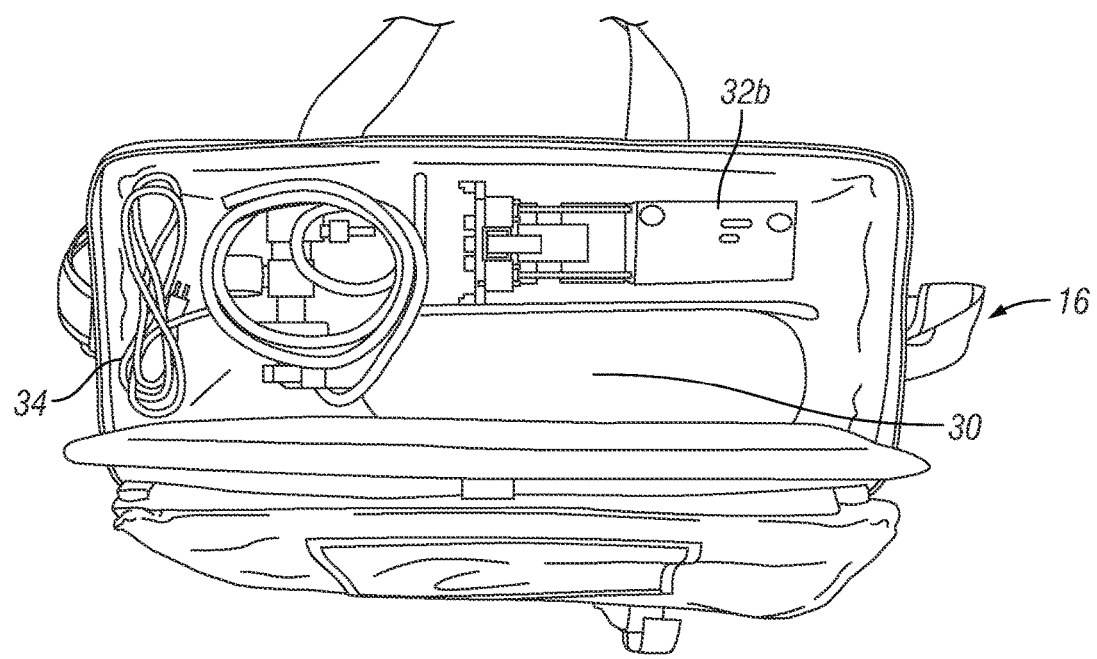
FIG. 1C is a top view of the clinical accessory kit of FIG. 1B in an opened configuration which reveals the kit's contents including: an AC power cord(s), a gas supply and an emergency drive device.
Figure 1D:
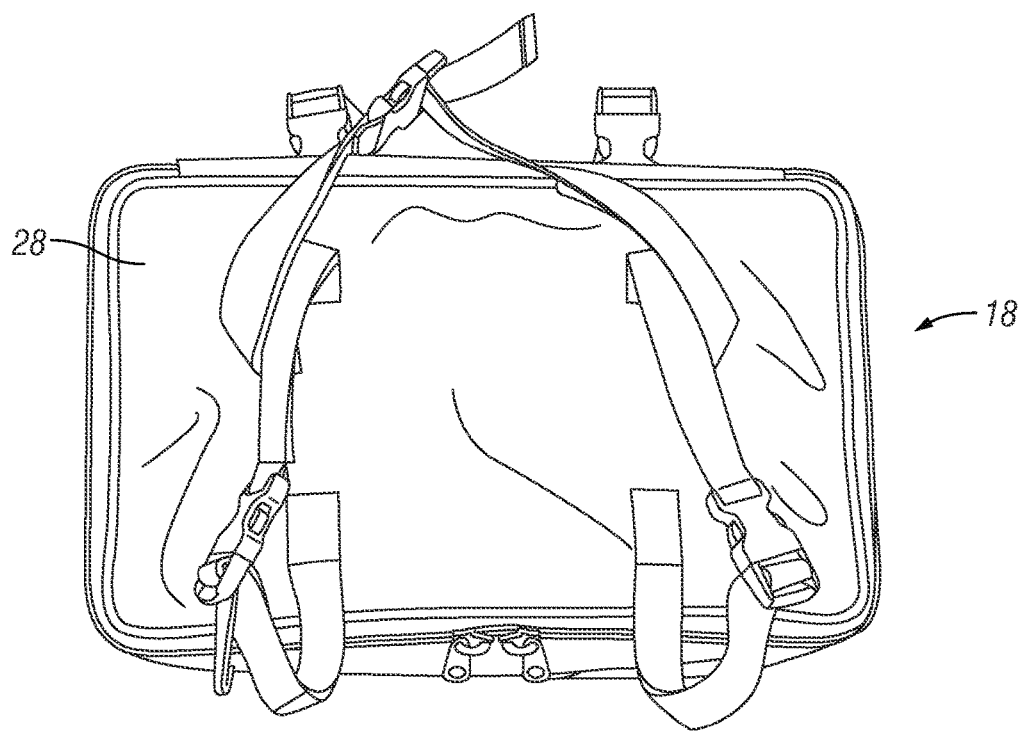
FIG. 1D is a side view of a transport accessory kit that may optionally be included in the system of FIG. 1A.
Figure 1E:
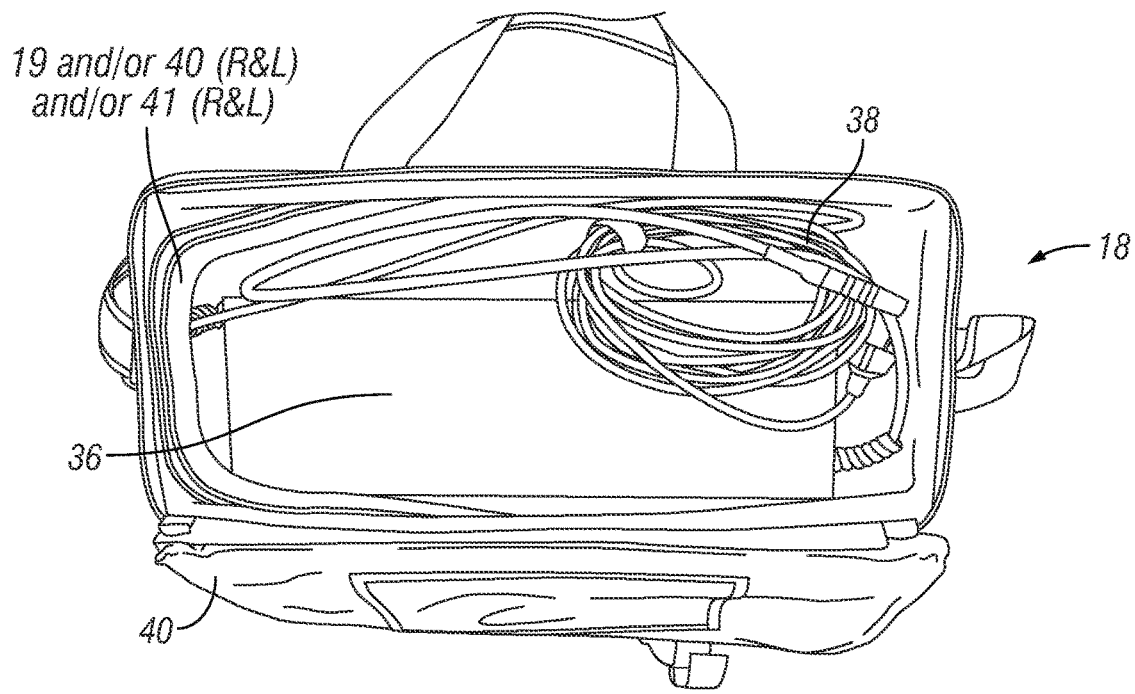
FIG. 1E is a top view of the transport accessory kit of FIG. 1D in an opened configuration which reveals the kit's contents including: transport power cord(s), strap(s) for attaching the transport kit to the extracorporeal life support device and a DC power supply device.

In some embodiments, the system 10 may include a clinical accessory kit 16, an example of which is seen in FIGS. 1B and 1C. Such clinical accessory kit 16 may comprises a housing or case 26, such hard or soft-sided bag, which contains accessories useable for operation of the ECLS device under routine conditions or in the event of non-routing conditions such as power outages or when an available source of compressed oxygen or oxygen enriched air is unavailable for operation of the device's oxygenator. In the example shown, the clinical accessories in the kit 16 include a compressed gas source 30, which may be a cylinder filed with 100% oxygen or other oxygen containing gas mixture suitable for use in operating the device's oxygenator. As an alternative to a gas filled cylinder as seen in FIG. 1C, the compressed gas source could comprise any other suitable source of oxygen such as an oxygen concentrator or a chemical oxygen generator. Oxygen concentrators typically concentrate oxygen from ambient air. Chemical oxygen generators normally use sodium chromate ($NaClO_3$) along with smaller amounts of other chemicals and convert this chemical to oxygen flow when the source is activated. The release of oxygen from the sodium chromate is accomplished by igniting the chemical. When converting the sodium chromate to oxygen a byproduct of the chemical reaction is heat. Thus, embodiments which employ a chemical oxygen generator may also include apparatus for dissipation or control of heat generated by the reaction. This clinical accessory kit 16 may also include a battery powered emergency drive 32b useable for driving a pump or other components of the ECLS device 10 in the event of a power outage or component failure. This emergency drive 32b may be battery or hand powered and useable to operate at least the blood pump and other critical components of the device 12 during a power outage or when other power is unavailable. Also, in this example, the clinical accessory kit 16 may include a power cord, e.g., an AC power cord, for connecting the device 10 to an electrical power outlet of the type typically available in hospitals or other buildings.

Figure 1F:
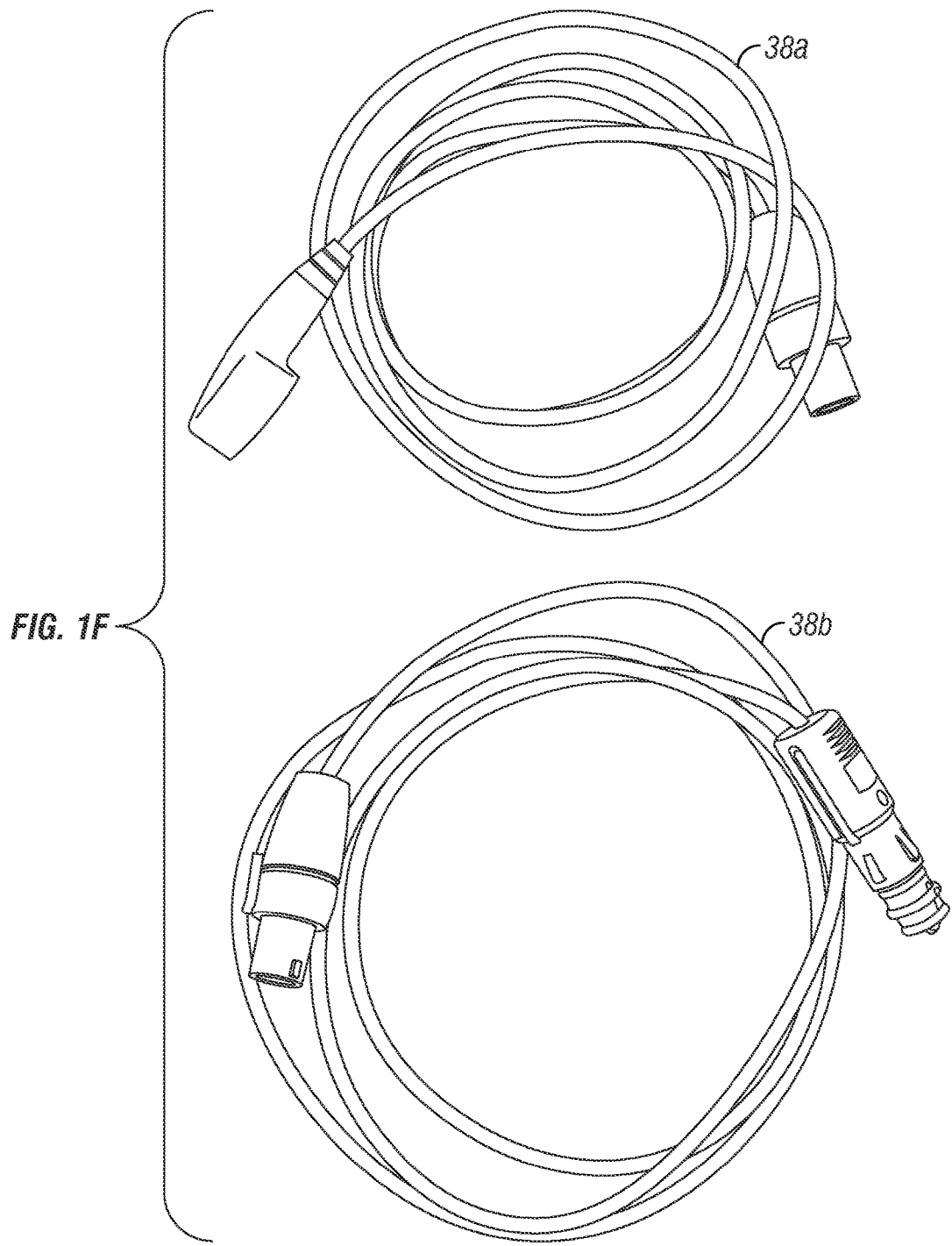
FIG. 1F shows examples of two types of transport power cords that may be included in the transport accessory kit to facilitate connecting the DC power supply to DC current outlets of a type commonly available in medical transport vehicles.

To facilitate its portability and transport, some embodiments of the system 10 may include a transport accessory kit 18, one example of which is seen in FIGS. 1D, 1E and 2A through 2B. In this example, the transport accessory kit 18 comprises a housing or case 28, such hard or soft-sided bag, which contains accessories useable during transport of the system 10. In this example, the accessories include a DC power supply 36, one or more transport power cord(s) 38 and strap(s) 19 or other attachment members useable for attaching the transport kit case or bag 28 to the ECLS device 12 during transit. The power cord(s) is/are useable for connecting the DC power supply 36 to a power outlet of the type commonly available in transport vehicles. The DC power supply 36 converts the voltage of the current received from the vehicle outlet to that used by the ECLS device 12, e.g., 31 VDC. FIG. 1F shows two examples of specialized transport power cords 38a, 38b that may be included in the transport accessory kit 18. Each of these specialized cords 38a and 38b is equipped with plug connectors configured for use with different types of DC electrical outlets found in many ground ambulances and helicopters. Power cord 38a is typically used in ground ambulances and power cord 38b is typically used in helicopters. The strap(s) 19 is/are useable for securing the transport kit case 28 to the ECLS device 12 in a manner shown in FIGS. 2A through 2B and described more fully herebelow.

Figure 2A:
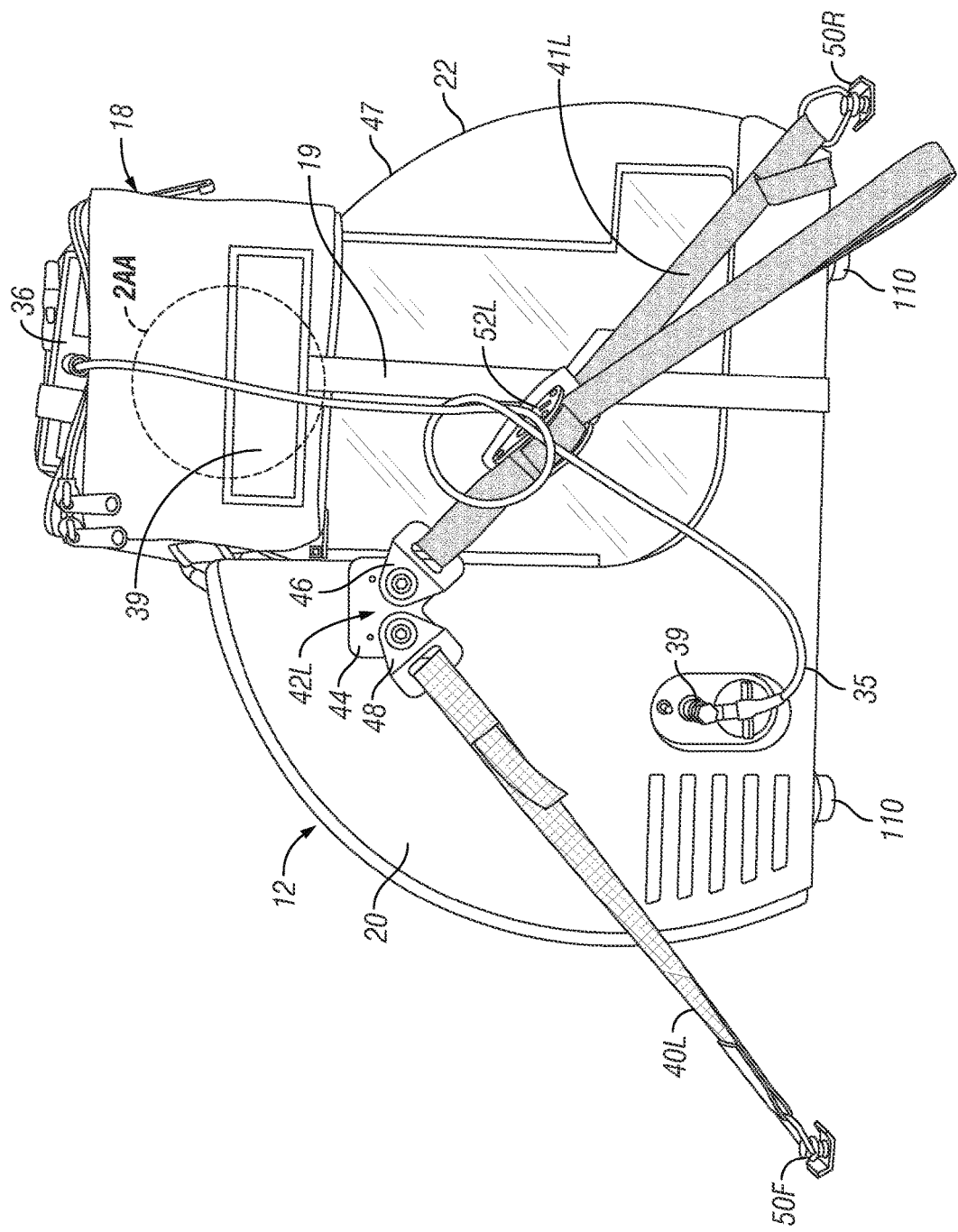
FIG. 2A is a right side view of the extracorporeal life support device of FIG. 1A equipped with anchoring belt assemblies having forward and aft anchoring belts for attaching the extracorporeal life support device to the floor of a transport vehicle and having the transport accessory kit of FIG. 1D attached to the top of the extracorporeal life support device.
Figure 2B:
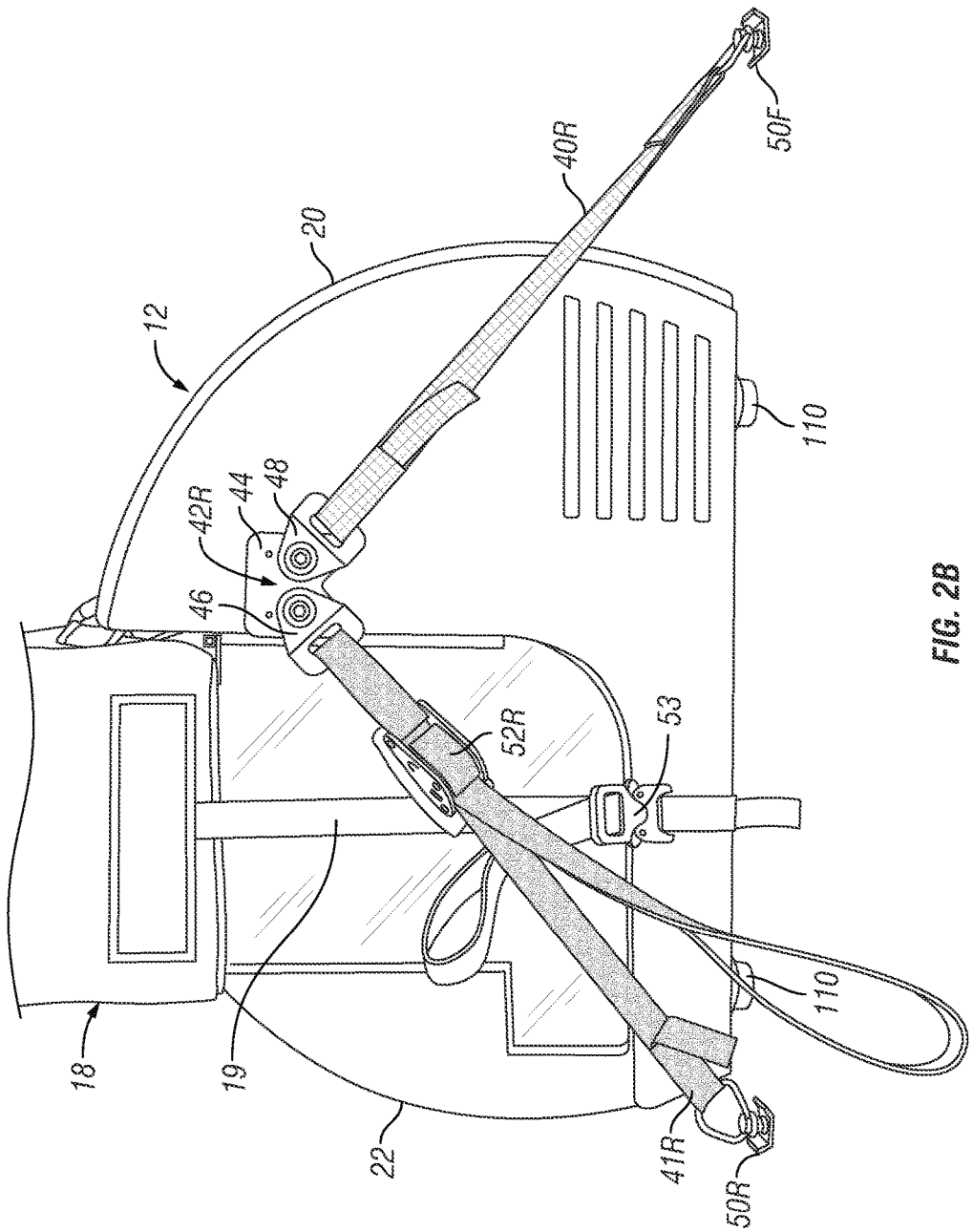
FIG. 2B is a left side view of the system of FIG. 2A.
Figure 2C:
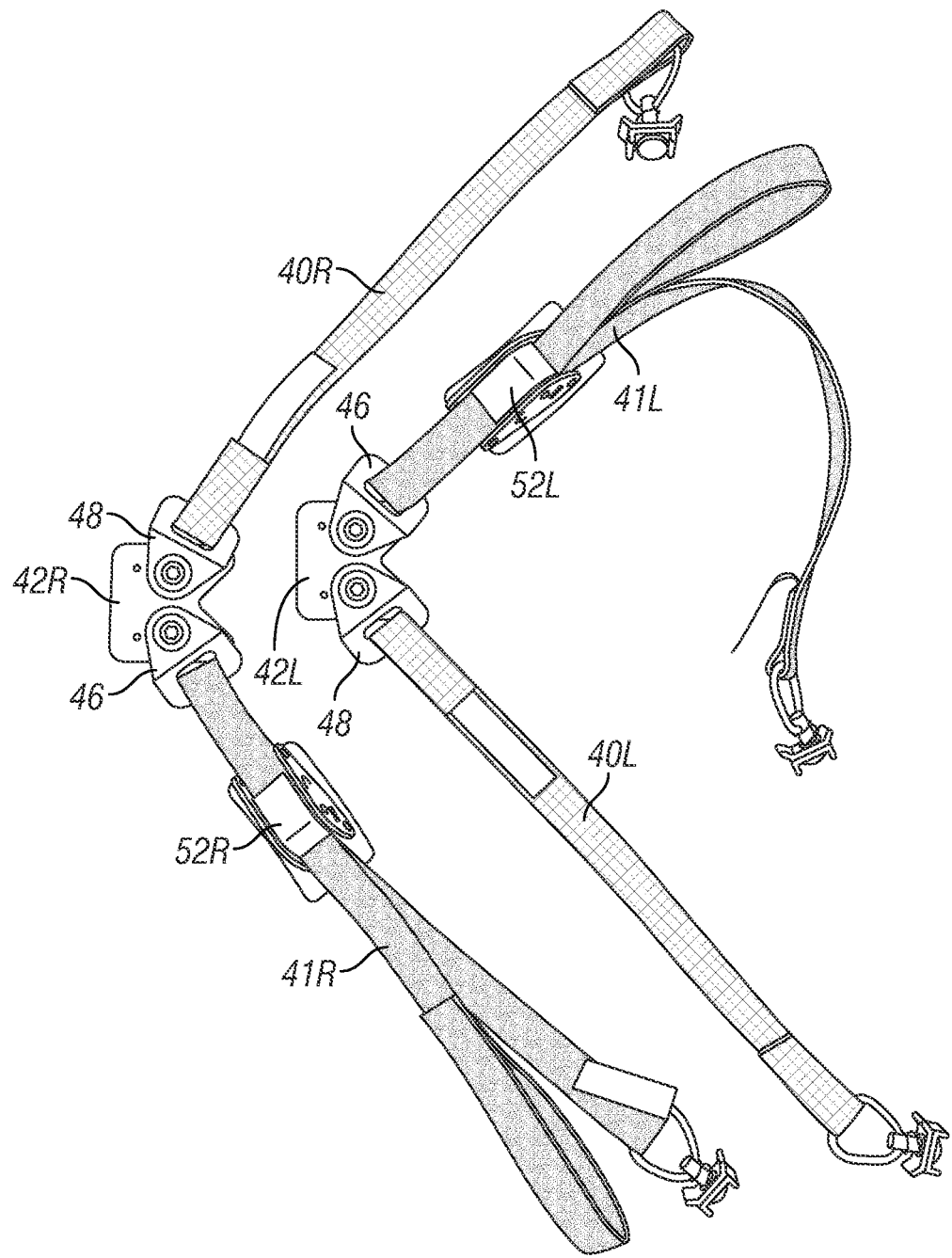
FIG. 2C shows the right and left anchoring belt assemblies used with the system shown in FIGS. 2A and 2B.

FIGS. 2A and 2B show right and left side views of the ECLS device 12 equipped with anchoring belt assemblies 42R, 42L and having the transport accessory kit 18 secured in a transport position on top of the ECLS device 12 by belt 19. FIGS. 2AA and 2AAA show details of the manner in which the transport accessory kit 18 is deployed and secured on top of the ECLS device 12. FIG. 2C shows the anchoring belt assemblies 42R, 42L separately.

As seen in FIGS. 2A and 2B, the anchoring belt assemblies 42R, 42L comprise first (e.g., forward) and second (e.g., rear) pivoting connectors 46, 48 which are attached securely to the right and left sides of the ECLS device 12. Each fixed-length first (e.g., forward) belt or other strap member 40R, 40L is attached at one end to the first pivoting connectors 48 on that side of the device 12 and each variable-length aft or rear belt or strap 41R, 41L is attached to the second pivoting connector 46 on that side of the device 12. The variable-length second belts 41R, 41L are equipped with adjustment mechanisms 52R, 52L useable for cinching or adjusting the length of the second belts 41R, 41L. Any suitable type of adjustment mechanism(s) may be used. Examples of suitable adjustment mechanisms include; Cam Buckle Anodized #75003 and Tie Down Stud #110218 available from Allsafe Jungfalk GmbH & Co. KG, Gerwigstraße 31, 78234 Engen, Germany. The first belts 40R, 40L are directed toward the front of the ECLS device where the controls used during transport are located.

During transport it is usually important for the front of the ECLS device 12 to be facing the transport caregiver who is at a caregiver location so that the caregiver when needed can easily access the controls. To avoid inadvertent placement of the ECLS device 12 in the inverted direction, the first belts or straps 40R, 40L may be color coded so as to be visually discernible from the second or rear belts or straps 41R, 41L. For example, the first belts 40R, 40L may be red and the second belts 41R, 41L may be black. In other embodiments, the first and/or second belts may include markings or other indicators to distinguish between the two types of belts. The ECLS device 12 itself may include markings or other indicators to ensure it is loaded into a transport vehicle in the proper orientation such that the front of the ECLS device 12 is facing the transport caregiver for ease of access to the controls.

In operation, as shown in FIGS. 2A and 2B, the anchoring belt assemblies 42R, 42L may be pre-attached to the sides of the ECLS device 12 or they may be stored elsewhere, such as in the transport kit case 28, and then attached to the sides of the ECLS device 12 when needed. Any suitable connection material or apparatus may be used for permanently or releasably connecting the anchoring belt assemblies 42R, 42L to the device 12. For example, the anchoring belt assemblies 42R, 42L may be connected to the ECLS device 12 via a quick connect or clipping mechanism, such as pins located on the back side of the belt assembly, or the backside of a bracket or pivoting connectors 46, 48 of the belt assemblies, which may be inserted into or coupled to corresponding holes or slots on the sides of the ECLS device 12. The anchoring belt assemblies 42R, 42L may be attached to the ECLS device 12 before or after loading the ECLS device 12 into a transport vehicle. When not attached to the ECLS device for transport, the with anchoring belt assemblies 42R, 42L may be disconnected and stored elsewhere, such as in the transport accessory kit housing or case 28. The back side of an attached anchoring belt assembly or its attachment bracket may optionally include pads or rubber puffers to reduce scratching.

The ECLS device 12, with its attached belt assemblies 42R, 42L, may be loaded into the transport vehicle along with the subject (or the harvested organ(s)) receiving treatment from the ECLS device 12. The color coding of the anchoring belts 40R, 40L, 41R, 41L may be observed and referenced to ensure that the ECLS device 12 is loaded into the vehicle in the right direction (i.e., with its front side facing in the direction of the caregiver's seat or usual location within the vehicle). This typically will require the first belts 40R, 40L to be directed toward the front of the vehicle and the second belts 41R, 41L to be directed toward the rear of the vehicle. Alternatively, the ECLS device may be loaded into the transport vehicle in the proper direction and the belt assemblies 42R, 42L, may subsequently be attached to the ECLS device.

After the ECLS device has been loaded into the transport vehicle, the free ends of the fixed-length first belts 40R, 40L are attached to desired first anchoring locations which are adjacent to one another at a first region of the floor or other surface(s) of the vehicle and the free ends of the variable-length second anchoring belts 41R, 41L are anchored to desired second anchoring locations which are adjacent to one another at a second region of the floor or other surface(s) of the vehicle. Thereafter, the adjustment mechanisms 52R, 52L are used to cinch or shorten the variable-length second anchoring belts 41R, 41L thereby causing the belts to be sufficiently taught to firmly hold the ECLS device 12 in position within the vehicle. In many instances, the floor of the transport vehicle will be equipped with recessed tracks and the free ends of the belts 40R, 40L, 41R, 41L will be equipped with hardware that allows them to be inserted into and affixed to desired locations within those recessed tracks, thereby establishing the appropriate anchoring locations for holding the ECLS device 12 in its intended position. In certain embodiments, one or more first belts may be a variable-length belt and one or more second or rear belts may be a fixed-length belt. In other embodiments, any combination of fixed-length and variable-length belts may be utilized for the first and/or the second or rear belts.

Additionally, to facilitate use of the ECLS device 12 during transport the securement belt 19 may be removed from the transport accessory kit 18 and used to attach the remainder of the transport accessory kit 18 to a transport position on top of the ECLS device 12, as seen in FIGS. 2A and 2B. To accomplish this, the user may lift a flap 39 at one end of the transport accessory case or bag 28 to expose a thru-slot or channel 25 that extends through the case or bag 28. The strap 19 may be fed through such slot or channel 25 and passed around the bottom of the ECLS device 12. The strap 19 is equipped with a cinching buckle 53 which is connected and used to cinch or shorten the strap 19 until the strap 19 is sufficiently taught to hold the transport kit case or bag 28 in the transport position on top of the ECLS device 12, as shown.

The appropriate power cord 38 is selected for use and removed from the transport kit case or bag 28 along with the DC power supply 36. One end of the selected power cord 38 is plugged into an electrical power outlet of the vehicle and the other end is plugged into an input jack of the DC power supply 36. The case or bag 28 may then be closed and the DC power supply placed on top of the case or bag 28 and held in place by straps 37 as shown in FIG. 2AAA. The power supply cord 35 of the DC power supply 36 is plugged into power input jack 39 of the ECLS device 12. Thus, the electrical current from an outlet in the transport vehicle is carried to the DC power supply 36 by a selected cord 38. The DC power supply then adjusts the voltage of the received power, as needed, and delivers the desired voltage of DC current through the power supply cord 35 to the ECLS device 12. The ECLS device 12 may be equipped with a battery backup to supply short term power to the device 12 during periods when it is not receiving externally sourced power through either the AC power supply 21 (typically used in hospital) or DC power supply (typically used in the transport vehicle).

As explained above, ECLS devices 12 of varying type and complexity may be used in conjunction with the transport facilitating kits, belt assemblies and other components/methods described herein. FIG. 3 shows a schematic component diagram 60 of one non-limiting example of an automated ECLS device 12 that may be used in some embodiments described herein. The components shown in this component diagram 60 include an inlet line 64, priming line 66 with clamp 74, reservoir 62 with blood level sensors 68, vent line 71 and vent pump 72, reservoir outlet line 80, blood pump 86, pump to oxygenator line 88, blood oxygenator 92, oxygenator to filer line 94, blood filter 98, outlet line 100 with bubble detector 102, fast clamp 104 and flow sensor 106, recirculation line 107 with shunt clamp 108 and controller C. Pressure sensors 70, 90 and 96 are also present on the reservoir vent line 71, pump to oxygenator line 88 and oxygenator to filter line 94, respectively. The controller C and monitoring unit MU are connected, by wired or wireless connectivity, to the user interface 24 as well as certain of the components 60. The monitoring unit MU may be programmed to receive and process signals from various sensor components. The controller C may be programmed to issue control signals to various operational components, thereby controlling operation of the ECLS device 12, as described herein.

In typical operation, the components 60 are initially filled with a priming fluid. Priming line clamp 74 may be opened and a suitable priming fluid, such as sterile 0.9% NaCl solution (saline), may be introduced through the priming line 66 while the controller C operates the pumps 72, 86 in a manner that fills all components with the priming fluid. As discussed in more detail below, during or after the priming process the controller C may cycle through certain pre-treatment tests, such as a system or performance test and a bubble detector test. A critical aspect of the operation of the system is to avoid inadvertent introduction of clinically significant gas emboli (e.g., bubbles) through the outlet line and into the patient's vasculature.

When it is desired to commence the ECLS treatment, the inlet line 64 is connected to the patient's vasculature, typically via a cannula that has been advanced to a central venous location such as the patient's vena cava or right atrium. The outlet line 100 is also connected to the patient's vasculature, typically via a cannula that has been advanced to a central arterial location such as the patient's aorta. The controller C causes the blood pump 86 to circulate blood through the system components 60 and, in at least cases where the patient is in cardiac arrest or has clinically insufficient cardiac output, the blood pump 86 creates sufficient flow and pressure to also circulate blood through the patient's vasculature. Incoming de-oxygenated blood fills the reservoir 62 and any gas that collects at the top of the reservoir due to degassing of the blood or other causes is removed through vent line 71 with or without active pumping by the vent pump 72. Deoxygenated blood from the reservoir 62 then flows though lines 80 and 88 into oxygenator 92. In the oxygenator, gas exchange occurs through membranes such that carbon dioxide is removed from the blood and oxygen is added to the blood. The resultant oxygenated blood then flows through line 94, through filter 98 and though the outlet line 100. The filter 98 captures any solid embolic material, such as small or microscopic blood clots, that may be present in the blood. In routine operation, the oxygenated blood flows though the outlet line, the bubble detector detects no bubbles, the fast clamp 104 remains open and the oxygenated blood flows into the patient's vasculature as intended. However, if the bubble detector 102 senses a bubble, it immediately sends a bubble detection signal to the monitoring unit MU and the controller C. In response to that bubble detection signal, the monitoring unit MU causes a bubble detection error signal to appear at the top of the display screen of user interface 24 and the controller C promptly issues control signals to the fast clamp 104 and shunt clamp 108 causing the fast clamp 104 to close before the detected bubble has flowed past it and causing shunt clamp 108 to open. As a result, the flow of blood into the patient ceases and the blood (including the detected air bubble) is shunted through recirculation line 107, through inlet line 64 and back into the reservoir 62. This recirculation continues until the detected bubble 9 (and any others) have been separated from the blood in reservoir 62 and ultimately removed through vent line 71. After the recirculation has proceeded for a desired period of time with no further bubbles being detected by the bubble detector 102, the controller C causes shunt clamp 108 to close and fast clamp 104 to open, thereby returning the system to its normal mode of operation with deoxygenated blood being removed from the patient's vasculature and oxygenated blood being returned into the patient's vasculature. It is important that the fast clamp 104 comprise a clamping or valving device that closes rapidly enough after a bubble is sensed by the bubble detector 102 to prevent the detected bubble from passing into the subject's vasculature. One example of a fast closing clamp useable in this application is that described in U.S. Pat. No. 7,367,540 (Brieske) entitled Fast Closing Clamp, the entire disclosure of which is expressly incorporated herein by reference.

During operation, running of the blood pump 86 and/or vent pump 72 causes negative pressure in the inlet line 64 and positive pressure in the outlet line 100. Occasionally, the negative pressure in the inlet line 64 may become excessive, especially if the overall amount of fluid in the extracorporeal circuit is low and the blood pump 86 is running at high speed. Excessive negative pressure in the inlet line 64 can have adverse consequences. For example, it may cause the tip of the inlet blood cannula to become suction-attached to the wall of the blood vessel in which it is positioned, potentially causing damage to the blood vessel. Also, the blood reservoir 62 could run dry or damages (e.g., leaks) could occur in system components 60. To deal with this potential problem, an additional pressure sensor (not shown) could optionally be present on the inlet line 64 and the Controller C could optionally be programmed to receive and process signals from that inlet line pressure sensor and, if the negative pressure in the inlet line exceeds a predetermined maximum, to issue control signals to the blood pump 86 and/or vent pump 72 causing the pump(s) 86 and/or 72 to reduce speed. This controlled reduction in pump speed will cause the venous pressure to rise in the inlet line until it reaches a desired pressure. This may be accomplished by any suitable programming of the controller C. One manner in which the controller C may be programmed to accomplish this is by Pressure Feedback Control with the following parameters:

Pressure Measurement Unit: mmHg
Pressure Measurement Update Interval: 300 ms
$K_p$ (proportional gain): 5
$K_i$ (integral gain): 1
$K_d$ (derivative gain): 0.6 (PV<SP)
$K_d$ (derivative gain): 0.3 (PV>SP)

Where:
PV=Process Variable (venous inlet pressure)
SP=Set point (venous inlet pressure limit)
$K_p$=Proportional gain
$K_i$=Integral gain
$K_d$=Derivative gain The derivative gain $K_d$ has two values because the speed of the blood pump should decrease very fast if the venous line gets kinked but the speed should increase only slowly if the operator changes the set point. In this example, the pressure feedback control is only active if the set limit of the blood pump is higher than 1500 rpm. A warning message is displayed, such as via a user interface 24, if the pressure feedback control does momentarily reduce the speed of the blood pump 86. Also, in this example, the pressure feedback control can be switched on/off, such as via a sensor settings menu on a user interface 24 but the default setting will be with the pressure feedback control switched on.

Any suitable pressure limits may be used. For example, the default value for the set limit of the deoxygenated blood pressure in inlet line 64 may be −120 mmHg. An indicator, such as a bar indicator on a user interface 24, may change appearance (e.g., change from green/red to grey) if the pressure feedback control is switched off. Neither the controller C nor monitoring unit MU supervise the venous pressure if the pressure feedback control is switched off.

The optional pressure feedback control described herein is not only useable in ECLS systems, but may be incorporated into any extracorporeal device or system that draws a body fluid (e.g., blood) from the body of a patient and is equipped with a pump and a controller. Examples of non-ECLS types of devices in which this pressure feedback control feature may be incorporated include but are not limited to devises used for apheresis, autotransfusion, hemodialysis, hemofiltration, plasmapheresis, photophoresis, etc.

ECLS devices 12 may also include modifications to the controller software aimed at streamlining the initial start-up and testing of the ECLS device. Specifically, as mentioned above, the ECLS device may include a controller C, which may be programmed to perform self-tests of the overall system performance and bubble detector and to display information and error signals in ways that facilitate rapid location and correction of any detected problems. FIGS. 4 through 9 are screen shots showing examples of information that may appear on the screen of the user interface 24 during preparation and pre-testing of the ECLS device 12. FIGS. 10A through 10D show enlarged views of the error signals associated with each of the screen shots shown in FIGS. 4 through 8.

Figure 4:
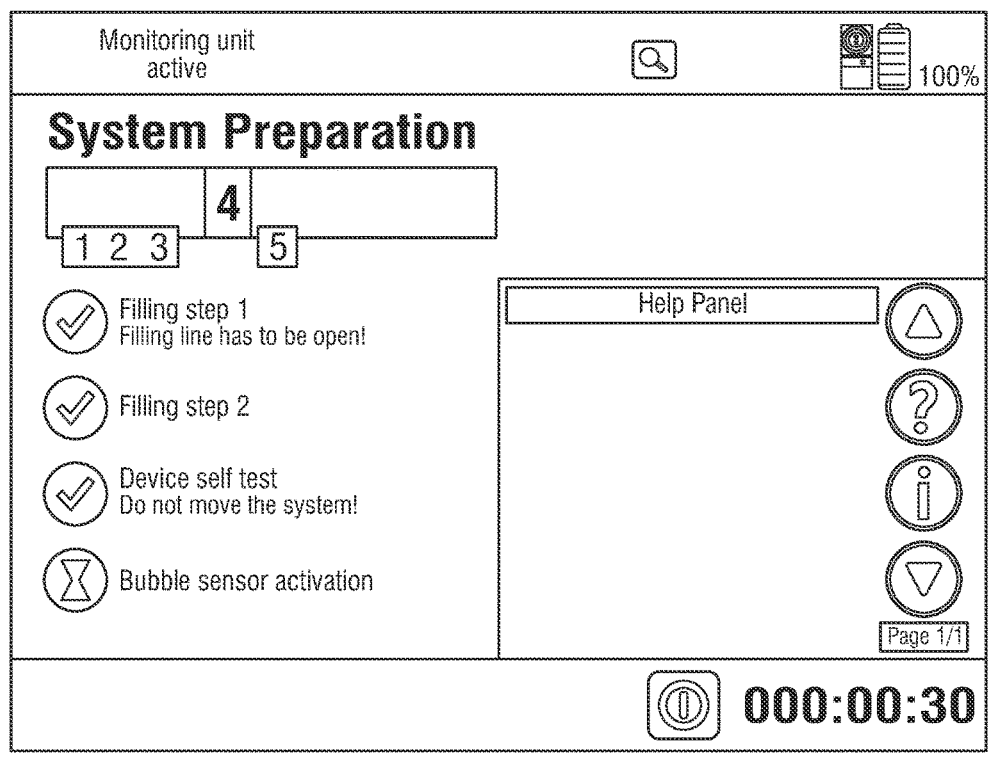
FIG. 4 is a screen shot showing an example of information that may appear on a user interface screen of an extracorporeal life support system during preparation and pre-testing of the system.
Figure 10B:
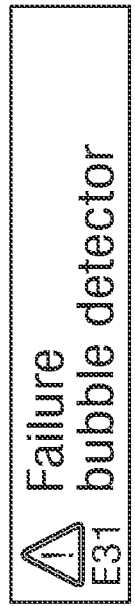
FIG. 10B shows another example of an error message that may be displayed on a user interface screen of an extracorporeal life support system when certain conditions are encountered during preparation and pre-testing of the system.
Figure 10D:
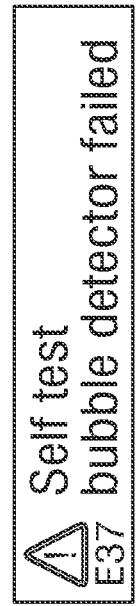
FIG. 10D shows another example of an error message that may be displayed on a user interface screen of an extracorporeal life support system when certain conditions are encountered during preparation and pre-testing of the system.
Figure 10A:
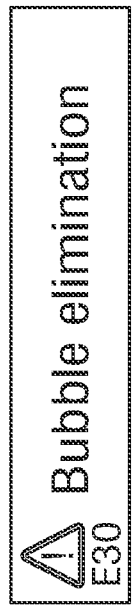
FIG. 10A shows an example of an error message that may be displayed on a user interface screen of an extracorporeal life support system when certain conditions are encountered during preparation and pre-testing of the system.

FIGS. 4 and 10A show information displayed on the screen of the user interface 24 during the device performance or system test. With reference to the device components shown in FIGS. 1A and 3, this performance or system test checks whether the device 12, after the patient module 22 has been fully filled with fluid, can generate pre-determined flow rates. The device 12 has clamps that directly affect the flow rate. Because of this, the performance test includes three separate test steps. In Step #1, flow is measured by flow sensor 106 while the blood pump 86 operates at constant speed with shunt clamp 108 open and fast clamp 104 open. Thereafter, in Step #2, flow is measured by flow sensor 106 while the blood pump 86 operates at constant speed with shunt clamp 108 open and fast clamp 104 closed. Thereafter, in Step #3, flow is measured by flow sensor 106 while the blood pump 86 operates at constant speed with shunt clamp 108 closed and fast clamp 104 closed. Both purge clamps 76, 78 are closed during all three steps of the performance test. The filling clamp 74 has no effect on the flow rate. All single fault error modes can be detected.

In the example shown, the system also performs a pre-test of the bubble sensor 102. The bubble sensor 102 has two independent channels. Two analog signals are transmitted from the bubble sensor 102 and are converted to square root signals. One square root signal gets evaluated by the controller C and the other square root signal gets evaluated by the monitoring unit MU. During filling of the patient module air in line 100 is displaced by liquid being pumped through the system by the blood pump 86. For certain types of blood pumps, this may occur as a single air to liquid transition. For other types of blood pumps, multiple air-liquid transitions may occur (i.e., air-liquid-air-liquid-, etc.) before a constant flow of liquid is achieved through line 100. Both square root signals may transit from permanent high (air) to a periodic square root signal (liquid). Every conceivable single fault error, like sensor errors or a cable break, may prevent this transition from happening on at least one evaluation unit. Therefore the result of the bubble sensor activation is very reliable and the patient module can be regarded as bubble free.

Figure 5:
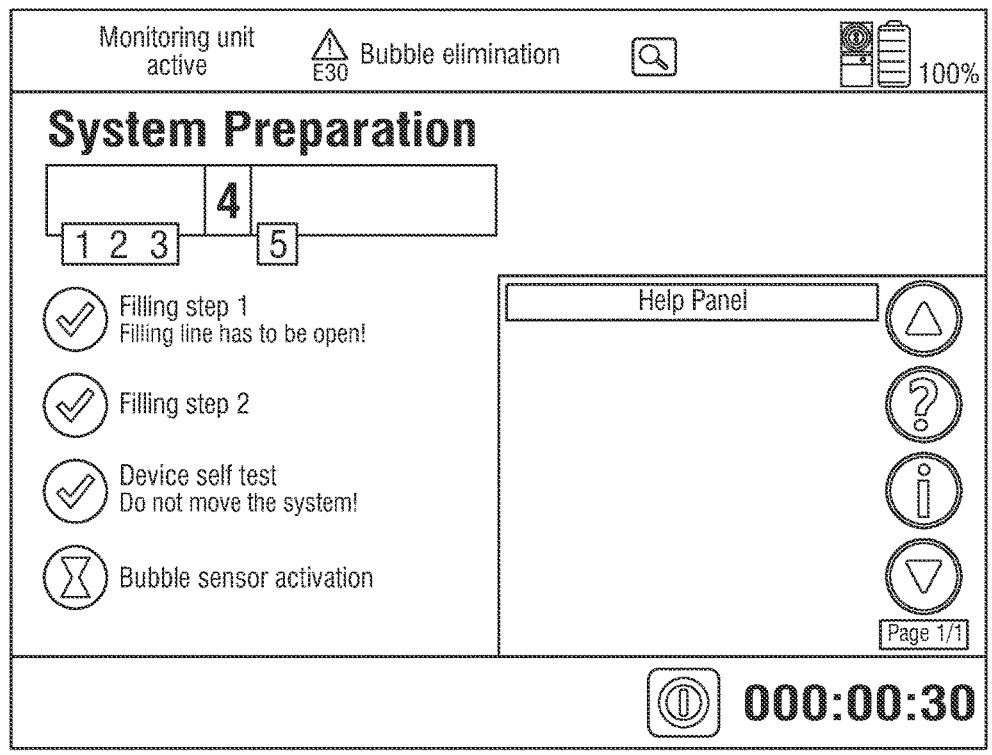
FIG. 5 is another screen shot showing an example of information that may appear on a user interface screen of an extracorporeal life support system during preparation and pre-testing of the system.

FIGS. 5 and 10A show information displayed on the screen of the user interface 24 when the bubble sensor 102 detects an air bubble after its activation. During the initial priming of the system, it is not unlikely for air bubbles to be detected. It is very likely that there are bubbles in the patient module. A sensor malfunction is still possible but, presuming that temperature has remained substantially constant, is unlikely because the bubble sensor 102 has previously passed the initial air/liquid transition test and the bubble sensor 102 is devoid of components that are likely to have degraded in the intervening time.

Figure 6:
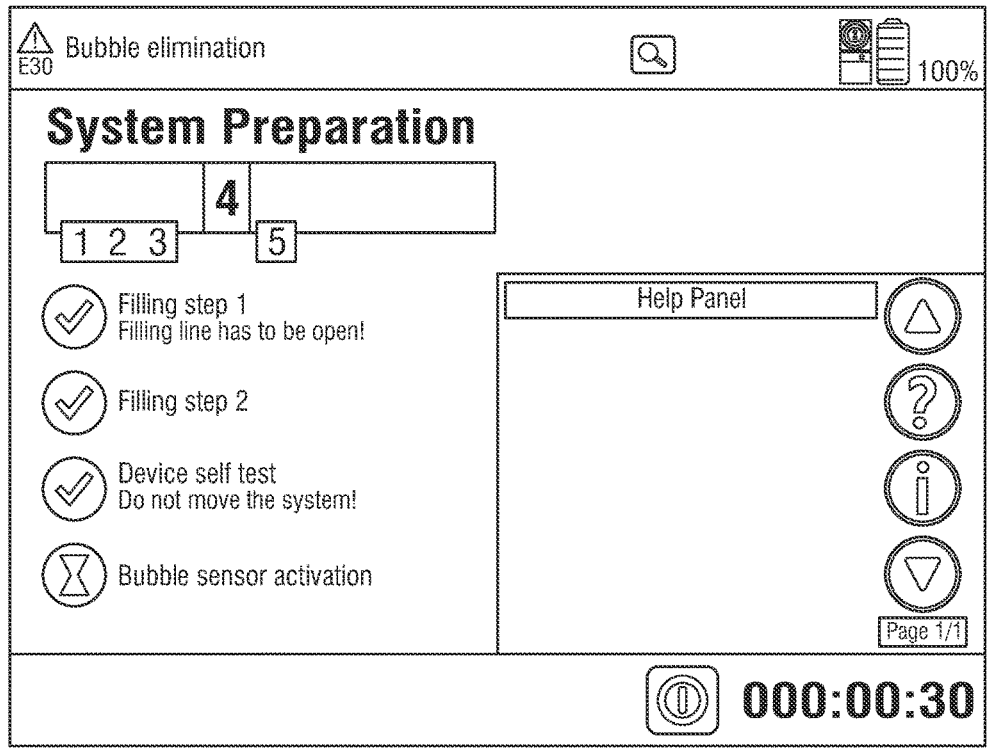
FIG. 6 is another screen shot showing an example of information that may appear on a user interface screen of an extracorporeal life support system during preparation and pre-testing of the system.

FIGS. 6 and 10B show information displayed on the screen of the user interface 24 when only the monitoring unit MU detects air bubbles after activation of the bubble sensor 102. This displayed information may result from different situations. For example, it may result if the attenuation of the analog signal on the signal path to the controller C and to the monitoring unit MU are not exactly the same. Therefore, if a small bubble at the detection limit gets detected by the monitoring unit MU but not by the controller C, the monitoring unit MU will start the bubble elimination procedure described herein. In other examples, there may be false alarms or the signal path to the controller C may become unable to detect air bubbles, but it is likely that there are bubbles in the patient module (e.g., approximately 50% of the time). This error mode may also indicate a circuit board malfunction because the result of the monitoring unit signal path and the control unit signal path do not match.

Figure 7:
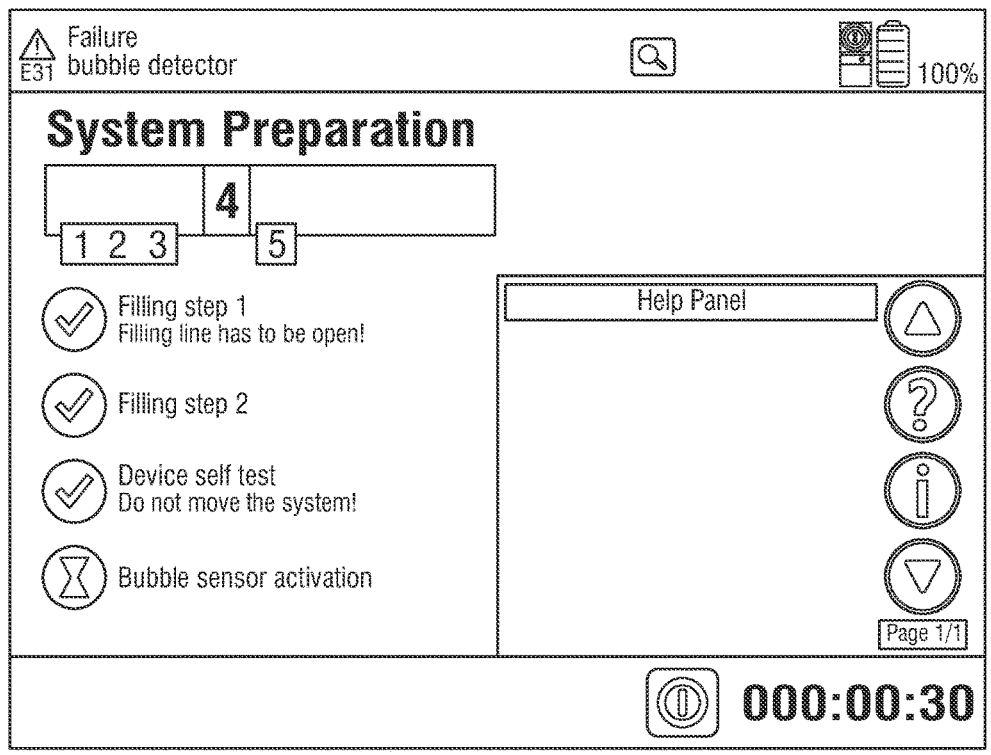
FIG. 7 is another screen shot showing an example of information that may appear on a user interface screen of an extracorporeal life support system during preparation and pre-testing of the system.
Figure 10C:
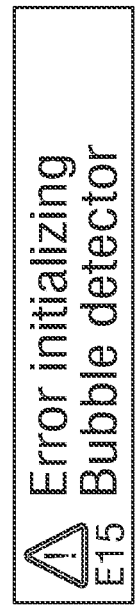
FIG. 10C shows another example of an error message that may be displayed on a user interface screen of an extracorporeal life support system when certain conditions are encountered during preparation and pre-testing of the system.

FIGS. 7 and 10C show information displayed on the screen of the user interface 24 when a malfunction of the bubble sensor 102 is detected during system preparation. This error message can be caused by two different error modes: Error mode 1: Permanent high signal on the signal path to the monitoring unit (no air/liquid transition has been detected so far); Error mode 2: Permanent low signal on the signal path to the monitoring unit (possible cable break). There is only one error message for both error modes because the end result for the user is the same, i.e., the bubble sensor is not working.

Figure 8:
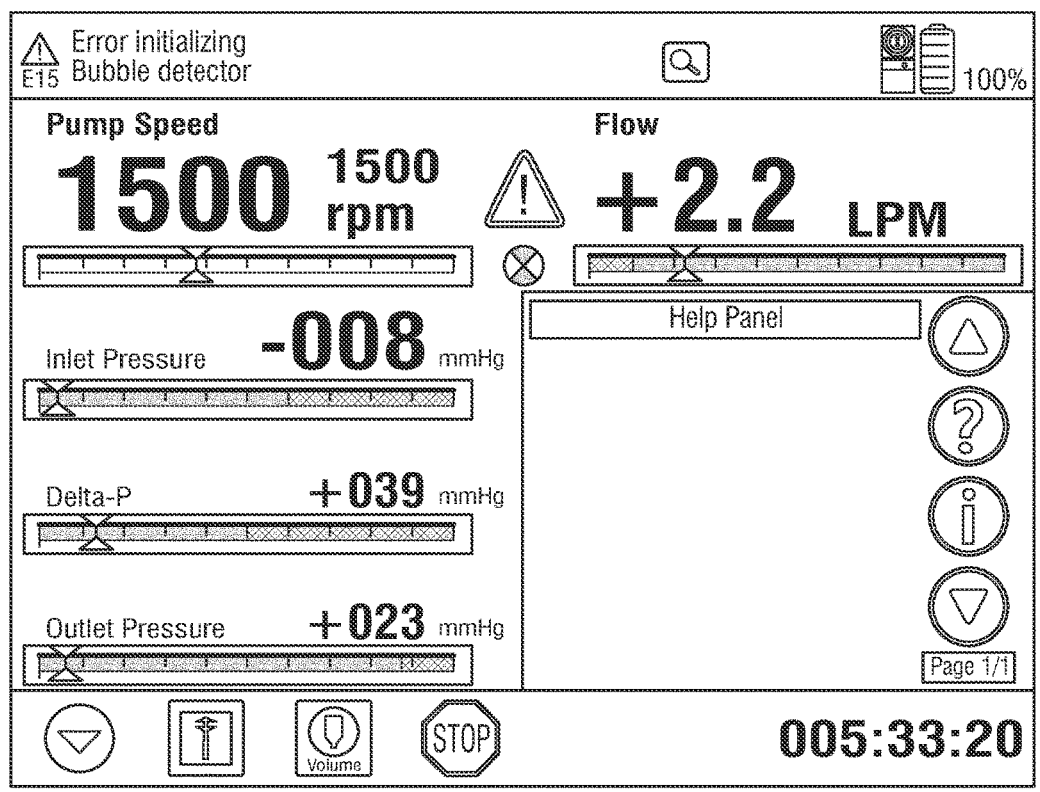
FIG. 8 is another screen shot showing an example of information that may appear on a user interface screen of an extracorporeal life support system during preparation and pre-testing of the system.

FIGS. 8 and 10D show information displayed on the screen of the user interface 24 when a malfunction of the bubble sensor 102 is detected after system preparation. A permanent square root signal on the signal path to the monitoring unit indicates that no air has been detected so far. This error mode may be triggered by a partially filled patient module. This could occur when the user connects and opens the filling line to the patient module before the device 12 is powered on. The square root signals indicate that the bubble sensor is working but the system was unable to perform a full self-test of the bubble sensor.

Figure 9:
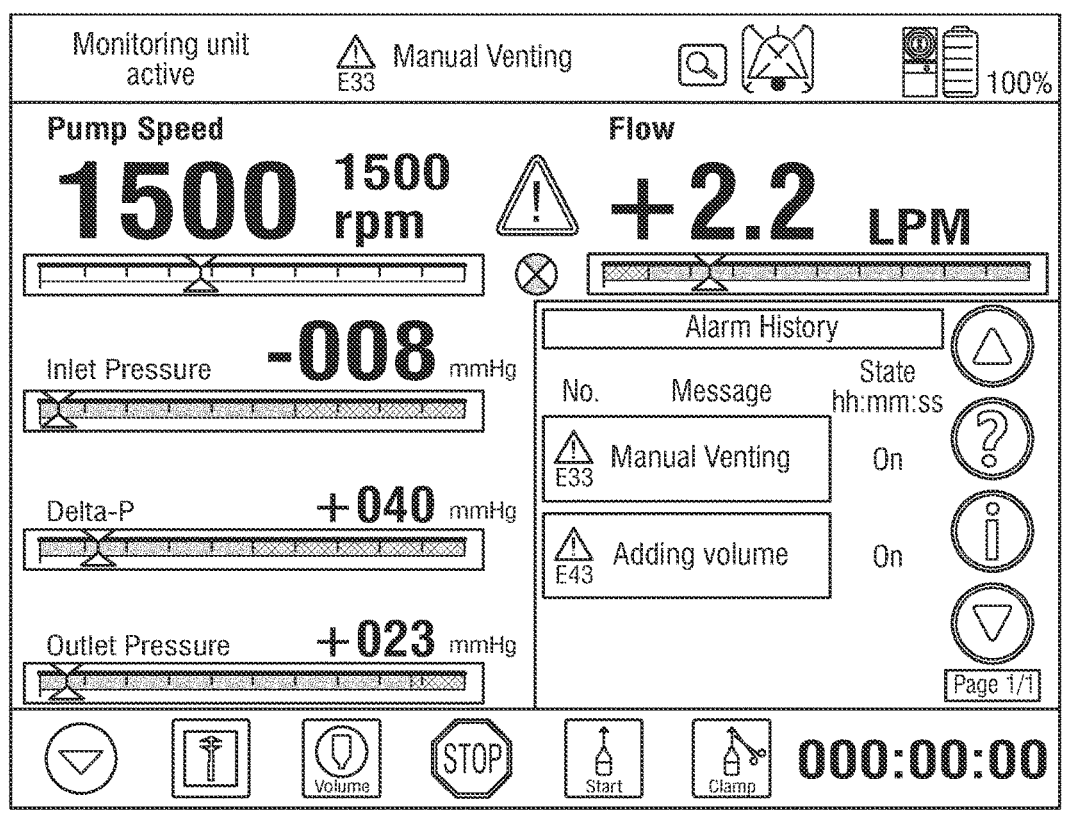
FIG. 9 is another screen shot showing an example of information that may appear on a user interface screen of an extracorporeal life support system during preparation and pre-testing of the system.

FIG. 9 shows information displayed on the screen of the user interface 24 when manual venting is performed.

In certain embodiments, the ECLS devices described herein may run for extended periods of time, e.g., up to 14 days, or longer than 14 days.

Figure 11:
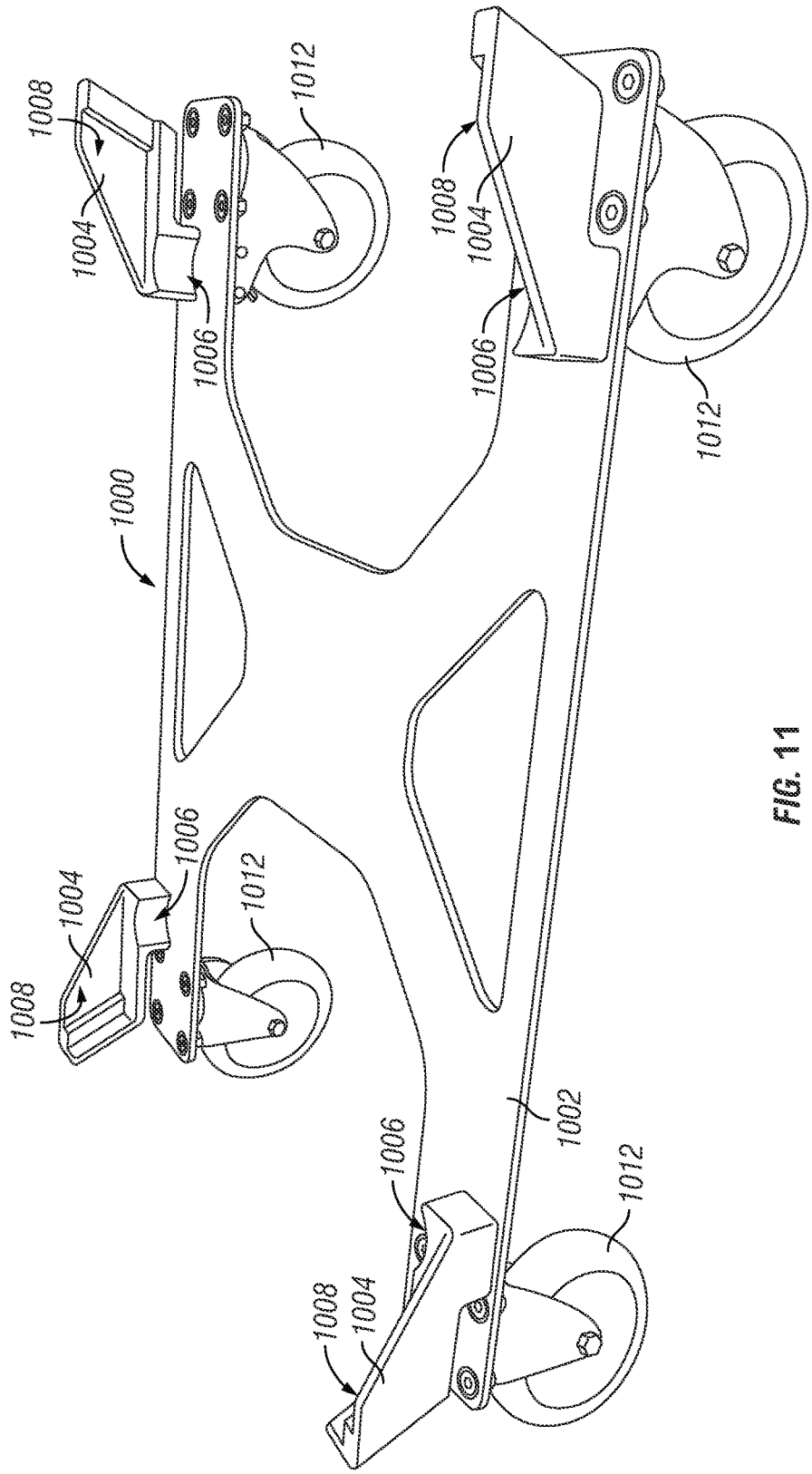
FIG. 11 is a perspective view of a cart device which may optionally be used in conjunction with an extracorporeal life support system.
Figure 12:
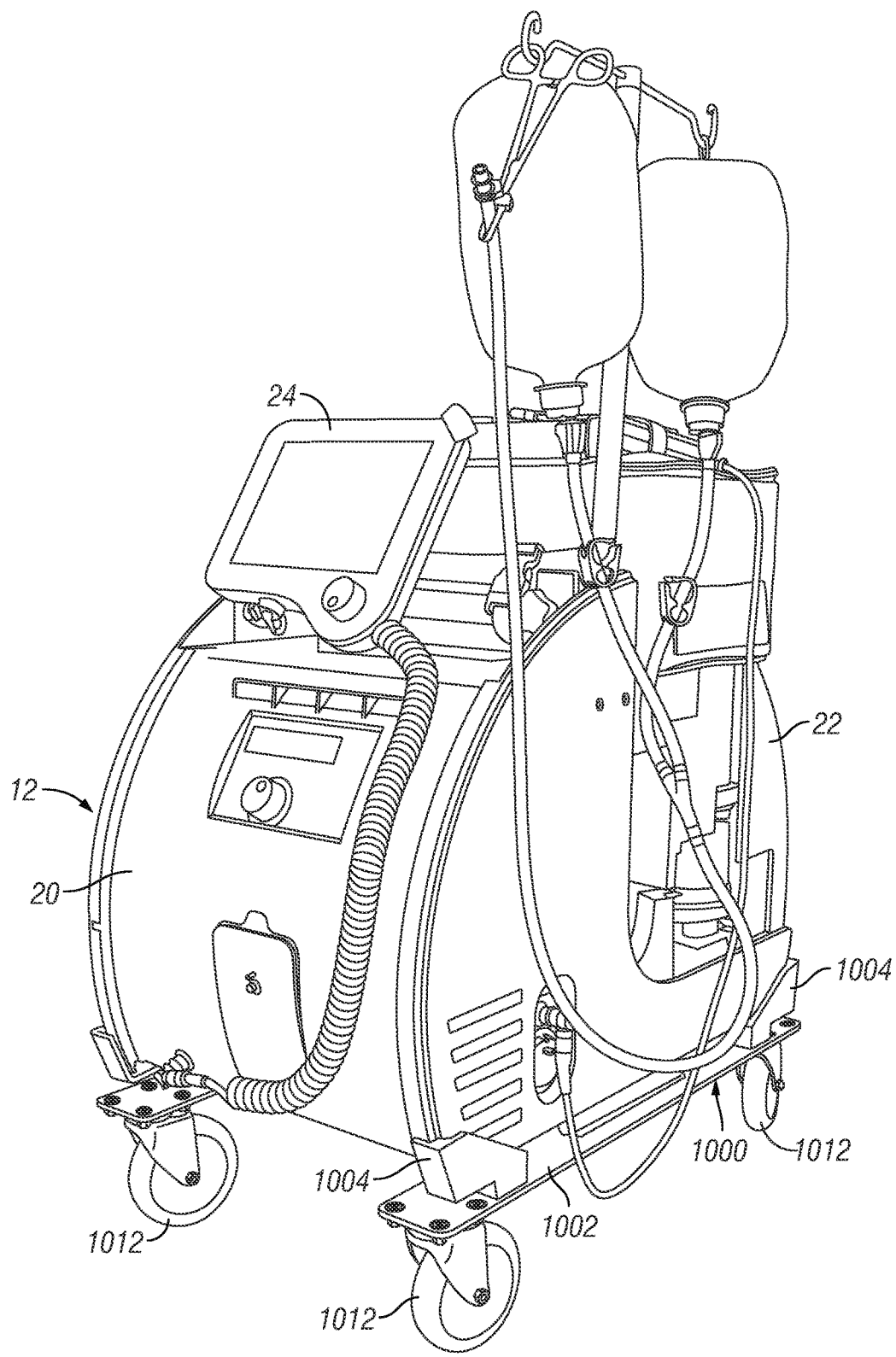
FIG. 12 is a perspective view of an extracorporeal life support device and transport accessory kit placed in a transport position in the cart of FIG. 11.

FIGS. 11 and 12 show a cart device 100 which may optionally be used for transporting the ECLS device 12 from a hospital building to a waiting transport vehicle or otherwise over an underlying floor or roadway surface. This cart 1000 comprises a frame 1002, a plurality of wheels 1012 attached to and extending downwardly from the frame and a plurality of engagement members 1004 attached to and extending upwardly from the frame 1002. The engagement members 1004 are located and configured so that the ECLS device 12 is positionable in a transport position (seen in FIG. 11) such that the bottom of the ECLS device 12 rests upon the frame 1002 and the engagement members 104 register against locations on the sides of the ECLS device 12 to prevent the ECLS device 12 from slipping or sliding off of the transfer cart. In the particular example shown, the cart has four corners and an engagement member 1004 is positioned on each of the four corners. In this example, the engagement members 1004 are configured to include upstanding regions 1008 which engage sides of the extracorporeal device as well as depressions or cut-out regions 1006 shaped to receive the legs 1010 of the ECLS device as it is lowered onto the cart. The abutment of the legs 1010 and side walls of the ECLS device 12 against the engagement members 104 allows one to push the cart/device combination along a floor or underlying surface while the ECLS 12 device 12 stays firmly mounted on the cart 1000. However, when it is desired to remove the ECLS device from the cart 1000, such as when it is being loaded into a transport vehicle, the device 12 can be lifted upwardly so that it no longer contacts the engagement members 1004 and is thereafter free of the cart 1000.

It is to be appreciated that, although the invention has been described hereabove with reference to certain examples or embodiments of the invention, various additions, deletions, alterations and modifications may be made to those described examples and embodiments without departing from the intended spirit and scope of the invention. For example, any elements, steps, members, components, compositions, reactants, parts or portions of one embodiment or example may be incorporated into or used with another embodiment or example, unless otherwise specified or unless doing so would render that embodiment or example unsuitable for its intended use. Also, where the steps of a method or process have been described or listed in a particular order, the order of such steps may be changed unless otherwise specified or unless doing so would render the method or process unsuitable for its intended purpose. Additionally, the elements, steps, members, components, compositions, reactants, parts or portions of any invention or example described herein may optionally exist or be utilized in the absence or substantial absence of any other element, step, member, component, composition, reactant, part or portion unless otherwise noted. All reasonable additions, deletions, modifications and alterations are to be considered equivalents of the described examples and embodiments and are to be included within the scope of the following claims.

What is claimed is:

1. A transport accessory kit usable to facilitate operation of an extracorporeal life support system having a front and a rear, during transport in a transport vehicle, the kit comprising:
    a right anchoring assembly attachable to a right side of the extracorporeal life support system;
    a left anchoring assembly attachable to a left side of the extracorporeal life support system;
    each of said right and left anchoring assemblies comprising:
        a forward pivoting connector attachable to the extracorporeal life support system;
        a fixed length forward belt or strap member which has first and second ends, the first end being connected to the forward pivoting connector and the second end being extendable toward the front of the system;
        an aft pivoting connector attachable to the extracorporeal life support system; and
        a variable length aft belt or strap member which has first and second ends, the first end being connected to the aft pivoting connector and the second end being extendable toward the rear of the system;
    wherein, after the system has been loaded into a transport vehicle, the second ends of the forward and aft belt or strap members are anchorable to the transport vehicle to hold the system in a position whereby the fixed length of the forward belt or strap members defines or limits a distance between the front of the system and a caregiver location within the transport vehicle.

2. A transport accessory kit according to claim 1 wherein the forward belt or strap members are visually distinguishable from the aft belt or strap members.

3. A transport accessory kit according to claim 2 wherein the forward belt or strap members are of a different color than the aft belt or strap members.

4. A transport accessory kit according to claim 1 wherein the extracorporeal life support system comprises a reusable module and a disposable module and wherein the right and left anchoring assemblies are connectable, respectively, to right and left sides of the reusable module.

5. A transport accessory kit according to claim 1 further comprising a right aft belt or strap member adjusting device and a left aft belt or strap member adjusting device for drawing taut the aft belt or strap members of said right and left anchoring assemblies after their second ends have been connected to the transport vehicle.

6. A transport accessory kit according to claim 1 wherein the kit further comprises one or more items selected from: one or more power cords for connecting the extracorporeal device to a power outlet in the transport vehicle; a DC power source; and one or more attachment members useable for attaching the transport accessory kit to the extracorporeal device.

7. A transport accessory kit according to claim 6 wherein the one or more power cords comprise at least two power cords having different types of plugs for use in different types of transport vehicle electrical outlets.

8. A transport accessory kit according to claim 7 wherein the power cord is useable for connecting the extracorporeal life support system to an electrical power outlet in a transport vehicle.

9. A transport accessory kit according to claim 6 wherein the power source comprises a DC battery power source useable for powering the extracorporeal life support system for a period of time.

10. A transport accessory kit according to claim 9 wherein the DC power source further comprises a power source cord for connecting the DC battery power source to the extracorporeal life support system.

11. A transport accessory kit according to claim 9 wherein the DC battery power source, when fully charged, is capable of powering the extracorporeal life support system for up to 60 minutes.

12. A transport accessory kit according to claim 1 wherein the transport accessory kit comprises a bag within which the right and left anchoring assemblies may be stored.

13. A transport accessory kit according to claim 1 further comprising a clinical accessory kit which comprises accessories useable for emergency operation of the extracorporeal life support system in the event of a loss of electrical power or loss of compressed oxygen.

14. A transport accessory kit according to claim 13 wherein the clinical accessory kit comprises at least one of a) a source of compressed oxygen, b) a battery operated emergency drive and c) a power cord.

15. A transport accessory kit according to claim 14 wherein the source of compressed oxygen is selected from i) a cylinder containing compressed oxygen; ii) an oxygen concentrator and iii) a chemical oxygen generator.

16. A transport accessory kit according to claim 1 in combination with an extracorporeal life support system which further comprises; an inlet which is connectable to vasculature of a human or animal subject or harvested organ(s); an outlet which is also connectable to the vasculature of the subject or organ(s); and gas exchange apparatus operable to a) receive deoxygenated blood from the vasculature via the inlet, b) oxygenate the blood and c) infuse the oxygenated blood into the vasculature via the outlet.

17. A method for using a transport accessory kit according to claim 1, said method comprising the steps of:
attaching the right anchoring assembly to a right side of the extracorporeal life support system;
attaching the left anchoring assembly to a left side of the extracorporeal life support system;
loading the extracorporeal life support system into the transport vehicle with the front of the extracorporeal life support system oriented toward said caregiver location and the rear of the extracorporeal life support system facing away from the caregiver location;
attaching the second ends of the fixed length forward belt or strap members to the transport vehicle;
attaching the second ends of the variable length aft belt or strap members to the transport vehicle;
adjusting the length of the aft belt or strap members, as needed, to draw taut all of the belt or strap members, thereby holding the extracorporeal life support system in the position within the vehicle.

18. A method according to claim 17 wherein a distance between the front of the extracorporeal life support system and the caregiver location is defined or limited by the fixed length of the drawn-taut forward belt or strap members, said distance allowing the caregiver to access controls of the extracorporeal life support system while seated in the caregiver location.

19. A method according to claim 17 further comprising the steps of:
loading a patient into the transport vehicle; and
using the extracorporeal life support system to treat the patient while the patient is in the transport vehicle.

20. A method according to claim 17 wherein the transport vehicle has an electrical power outlet and wherein the transport accessory kit further comprises a power cord useable for connecting the extracorporeal life support system to the electrical power outlet in the transport vehicle, and wherein the method further comprises the step of:
using the power cord to connect the extracorporeal life support system to the electrical power outlet in the transport vehicle.

* * * * *